(12) United States Patent
Hernandez-Torres et al.

(10) Patent No.: US 9,718,729 B2
(45) Date of Patent: *Aug. 1, 2017

(54) BIOCIDES FOR BIO-BASED BINDERS, FIBROUS INSULATION PRODUCTS AND WASH WATER SYSTEMS

(75) Inventors: Jesus M. Hernandez-Torres, Pataskala, OH (US); Liang Chen, New Albany, OH (US); William R. Cooper, Johnstown, OH (US)

(73) Assignee: Owens Corning Intellectual Capital, LLC, Toledo, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 13/026,415

(22) Filed: Feb. 14, 2011

(65) Prior Publication Data

US 2011/0200814 A1    Aug. 18, 2011

Related U.S. Application Data

(63) Continuation-in-part of application No. 12/900,540, filed on Oct. 8, 2010, now Pat. No. 8,864,893, and a
(Continued)

(51) Int. Cl.
*C03C 25/26* (2006.01)
*A01N 25/34* (2006.01)
(Continued)

(52) U.S. Cl.
CPC .............. *C03C 25/26* (2013.01); *A01N 25/04* (2013.01); *A01N 25/34* (2013.01);
(Continued)

(58) Field of Classification Search
CPC ..... C08K 5/0025; C08K 5/0058; C08L 33/02; A01N 25/34; A01N 25/04
See application file for complete search history.

(56) References Cited

U.S. PATENT DOCUMENTS

| 2,407,548 A | 9/1946 | Goldman |
| 3,416,288 A | 12/1968 | Coons |

(Continued)

FOREIGN PATENT DOCUMENTS

| CN | 101203555 | 6/2008 |
| CN | 101218186 | 7/2008 |

(Continued)

OTHER PUBLICATIONS

Arch Chemicals, Building Products Biocide Selection Guide, Mar. 12, 2006.*

(Continued)

*Primary Examiner* — Frank Vineis
(74) *Attorney, Agent, or Firm* — Calfee, Halter & Griswold LLP

(57) ABSTRACT

Biocides for bio-based binder compositions are disclosed. Bio-based binders include those having a nutrient source such as carbohydrate, protein or fat, which can serve as an energy source for organisms to grow in areas that contact binder. Principal areas that contact bio-based binder in a fiberglass insulation manufacturing process include the raw ingredients, the binder chemicals, the prepared binder dispersions, the forming hood and related equipment, the final insulation product and, importantly, the cleaning systems and washwater arising from cleaning the manufacturing equipment and/or forming the product. Frequently the washwater is stored until re-cycled for re-use. Storage may take place in tanks, towers, vats and even outdoor reservoirs, all of which may harbor the growth of unwanted organisms, for which a biocide is desirable.

10 Claims, 3 Drawing Sheets

Related U.S. Application Data continuation-in-part of application No. 12/776,703, filed on May 10, 2010, now abandoned.

(60) Provisional application No. 61/250,187, filed on Oct. 9, 2009, provisional application No. 61/178,745, filed on May 15, 2009.

(51) Int. Cl.

| | | |
|---|---|---|
| *C09J 103/02* | (2006.01) | |
| *A01N 25/04* | (2006.01) | |
| *C03C 25/10* | (2006.01) | |
| *C03C 25/28* | (2006.01) | |
| *C03C 25/32* | (2006.01) | |
| *C08K 5/00* | (2006.01) | |
| *C09J 105/06* | (2006.01) | |
| *C03C 25/14* | (2006.01) | |

(52) U.S. Cl.
CPC ........ *C03C 25/1095* (2013.01); *C03C 25/146* (2013.01); *C03C 25/285* (2013.01); *C03C 25/321* (2013.01); *C08K 5/0058* (2013.01); *C09J 103/02* (2013.01); *C09J 105/06* (2013.01); *Y10T 428/249924* (2015.04)

(56) References Cited

U.S. PATENT DOCUMENTS

| | | | |
|---|---|---|---|
| 3,669,638 A | 6/1972 | Wong et al. | |
| 3,705,073 A | 12/1972 | Marzocchi et al. | |
| 3,759,854 A | 9/1973 | Chang et al. | |
| 3,842,977 A | 10/1974 | Hollander | |
| 3,944,690 A | 3/1976 | Distler et al. | |
| 4,052,257 A | 10/1977 | Hill et al. | |
| 4,054,713 A | 10/1977 | Sakaguchi et al. | |
| 4,324,833 A | 4/1982 | Yau | |
| 5,055,428 A | 10/1991 | Porter | |
| 5,077,361 A | 12/1991 | Hughes et al. | |
| 5,116,890 A | 5/1992 | Floyd et al. | |
| 5,134,160 A * | 7/1992 | Whitekettle et al. | 514/479 |
| 5,208,075 A | 5/1993 | Kroner et al. | |
| 5,284,700 A | 2/1994 | Strauss et al. | |
| 5,318,990 A | 6/1994 | Strauss | |
| 5,321,064 A | 6/1994 | Vaidya et al. | |
| 5,340,868 A | 8/1994 | Straus et al. | |
| 5,346,947 A | 9/1994 | Guerro et al. | |
| 5,371,140 A | 12/1994 | Parks | |
| 5,393,335 A | 2/1995 | Puckett et al. | |
| 5,430,070 A | 7/1995 | Kono | |
| 5,446,078 A | 8/1995 | Vaidya et al. | |
| 5,480,963 A | 1/1996 | Jiang et al. | |
| 5,523,264 A | 6/1996 | Mattson | |
| 5,565,254 A | 10/1996 | Norvell | |
| 5,582,682 A | 12/1996 | Ferretti | |
| 5,635,123 A | 6/1997 | Riebel et al. | |
| 5,661,213 A | 8/1997 | Arkens et al. | |
| 5,714,264 A | 2/1998 | Sacharski et al. | |
| 5,888,292 A | 3/1999 | Tremblay | |
| 5,895,804 A | 4/1999 | Lee et al. | |
| 5,932,499 A | 8/1999 | Xu et al. | |
| 5,983,598 A | 11/1999 | Quinones | |
| 6,182,422 B1 | 2/2001 | Andersen et al. | |
| 6,221,973 B1 | 4/2001 | Arkens et al. | |
| 6,274,661 B1 | 8/2001 | Chen et al. | |
| 6,331,350 B1 | 12/2001 | Taylor et al. | |
| 6,369,104 B1 * | 4/2002 | Kleina et al. | 514/528 |
| 6,399,694 B1 | 6/2002 | McGrath et al. | |
| 6,439,383 B1 | 8/2002 | Janousek | |
| 6,447,596 B1 | 9/2002 | Tremblay et al. | |
| 6,527,014 B1 | 3/2003 | Aubourg | |
| 6,613,152 B1 | 9/2003 | Maas et al. | |
| 6,669,945 B1 | 12/2003 | Nardin et al. | |
| 6,878,455 B2 | 4/2005 | Kunzel et al. | |
| 6,884,849 B2 | 4/2005 | Chen et al. | |
| 6,890,666 B2 | 5/2005 | Kunzel et al. | |
| 6,933,349 B2 | 8/2005 | Chen et al. | |
| 7,026,390 B2 | 4/2006 | O'Brien Bernini et al. | |
| 7,141,626 B2 | 11/2006 | Rodrigues et al. | |
| 7,258,802 B2 | 8/2007 | Miks | |
| 7,754,020 B2 | 7/2010 | Cline et al. | |
| 7,772,347 B2 | 8/2010 | Swift et al. | |
| 7,780,858 B2 | 8/2010 | Miks | |
| 7,803,879 B2 | 9/2010 | Srinivasan et al. | |
| 7,807,771 B2 | 10/2010 | Swift et al. | |
| 7,829,197 B2 | 11/2010 | Chen et al. | |
| 7,829,611 B2 | 11/2010 | Kelly | |
| 7,842,382 B2 | 11/2010 | Helbing | |
| 7,854,980 B2 | 12/2010 | Jackson et al. | |
| 7,893,154 B2 | 2/2011 | Van Herwijnen et al. | |
| 7,935,274 B2 | 5/2011 | Schlosser | |
| 8,053,049 B2 | 11/2011 | Ruid et al. | |
| 8,197,587 B2 | 6/2012 | Jaffrennou et al. | |
| 8,569,315 B2 * | 10/2013 | Sianawati | A01N 47/12 424/400 |
| 8,864,893 B2 * | 10/2014 | Hawkins et al. | 106/215.5 |
| 8,980,807 B2 | 3/2015 | Hora et al. | |
| 2001/0033926 A1 | 10/2001 | Matthews et al. | |
| 2002/0182965 A1 | 12/2002 | Snyder | |
| 2002/0188055 A1 | 12/2002 | Chen et al. | |
| 2003/0008978 A1 | 1/2003 | Chen et al. | |
| 2003/0022580 A1 | 1/2003 | Bogrett et al. | |
| 2003/0181602 A1 | 9/2003 | Ansmann et al. | |
| 2004/0001963 A1 | 1/2004 | Watanabe et al. | |
| 2004/0043686 A1 * | 3/2004 | Batdorf | A01N 25/34 442/123 |
| 2004/0103604 A1 | 6/2004 | Kunzel et al. | |
| 2004/0116016 A1 * | 6/2004 | Delaviz et al. | 442/123 |
| 2004/0122166 A1 | 6/2004 | O'Brien et al. | |
| 2004/0254285 A1 | 12/2004 | Rodrigues et al. | |
| 2005/0070186 A1 | 3/2005 | Shoemake | |
| 2005/0084675 A1 | 4/2005 | Wang | |
| 2005/0170721 A1 * | 8/2005 | Toas et al. | 442/149 |
| 2005/0192390 A1 | 9/2005 | Dobrowolski et al. | |
| 2005/0215153 A1 | 9/2005 | Cossement et al. | |
| 2005/0260368 A1 | 11/2005 | Ruid et al. | |
| 2005/0284065 A1 | 12/2005 | Shaffer | |
| 2006/0057365 A1 | 3/2006 | Swoboda et al. | |
| 2006/0111480 A1 | 5/2006 | Hansen et al. | |
| 2006/0178064 A1 | 8/2006 | Balthes et al. | |
| 2006/0252855 A1 | 11/2006 | Pisanova et al. | |
| 2006/0252955 A1 | 11/2006 | Pisanova et al. | |
| 2007/0010651 A1 | 1/2007 | Finech et al. | |
| 2007/0014995 A1 | 1/2007 | Chacko et al. | |
| 2007/0027283 A1 | 2/2007 | Swift et al. | |
| 2007/0036975 A1 | 2/2007 | Miele et al. | |
| 2007/0054082 A1 | 3/2007 | Beyer et al. | |
| 2007/0287019 A1 | 12/2007 | Chen et al. | |
| 2008/0051539 A1 * | 2/2008 | Kelly | 526/199 |
| 2008/0108741 A1 | 5/2008 | Van Herwijnen et al. | |
| 2008/0115460 A1 | 5/2008 | Ruid et al. | |
| 2008/0156041 A1 | 7/2008 | Cooper | |
| 2008/0216450 A1 | 9/2008 | MacLeod et al. | |
| 2008/0281285 A1 | 11/2008 | Noda et al. | |
| 2009/0020448 A1 | 1/2009 | Emond | |
| 2009/0068416 A1 | 3/2009 | Noda et al. | |
| 2009/0080938 A1 | 3/2009 | Nagamine | |
| 2009/0098387 A1 | 4/2009 | Brady et al. | |
| 2009/0156080 A1 | 6/2009 | Finch et al. | |
| 2009/0169867 A1 | 7/2009 | Kelly | |
| 2009/0170978 A1 | 7/2009 | Kelly | |
| 2009/0275699 A1 | 11/2009 | Zhang et al. | |
| 2009/0324915 A1 | 12/2009 | Swift et al. | |
| 2010/0048813 A1 | 2/2010 | Clauss et al. | |
| 2010/0063166 A1 | 3/2010 | Behler | |
| 2010/0147032 A1 | 6/2010 | Chacko et al. | |
| 2010/0203790 A1 | 8/2010 | Moulton et al. | |
| 2010/0222463 A1 | 9/2010 | Brady et al. | |
| 2010/0242402 A1 | 9/2010 | Briner et al. | |
| 2010/0282996 A1 | 11/2010 | Jaffrennou et al. | |
| 2010/0300983 A1 | 12/2010 | Miks | |
| 2010/0301256 A1 | 12/2010 | Hampson et al. | |
| 2010/0305271 A1 | 12/2010 | Mentink et al. | |
| 2010/0310867 A1 | 12/2010 | VanHerwijnen et al. | |

(56) References Cited

U.S. PATENT DOCUMENTS

| | | |
|---|---|---|
| 2010/0320113 A1 | 12/2010 | Swift |
| 2011/0003522 A1 | 1/2011 | Chen et al. |
| 2011/0021101 A1 | 1/2011 | Hawkins et al. |
| 2011/0060095 A1 | 3/2011 | Tutin et al. |
| 2011/0086567 A1 | 4/2011 | Hawkins |
| 2011/0091710 A1 | 4/2011 | Mirth et al. |
| 2011/0100256 A1 | 5/2011 | Anderson et al. |
| 2011/0210280 A1 | 9/2011 | Jaffrennou et al. |
| 2011/0223364 A1 | 9/2011 | Hawkins |
| 2012/0065417 A1 | 3/2012 | Hora et al. |
| 2012/0070645 A1 | 3/2012 | Jaffrennou et al. |
| 2012/0122758 A1 | 5/2012 | Andjelic et al. |
| 2012/0133073 A1 | 5/2012 | Pacorel et al. |
| 2012/0144868 A1 | 6/2012 | Mirth et al. |
| 2013/0023174 A1 | 1/2013 | Quinn et al. |
| 2013/0065803 A1 | 3/2013 | Hora et al. |
| 2013/0067861 A1 | 3/2013 | Turner |
| 2013/0211068 A1 | 8/2013 | Anderson et al. |
| 2014/0038485 A1 | 2/2014 | Anderson et al. |
| 2014/0051824 A1 | 2/2014 | Anderson et al. |
| 2014/0083328 A1 | 3/2014 | Lochel, Jr. et al. |
| 2015/0152244 A1 | 6/2015 | Hernandez-Torres |

FOREIGN PATENT DOCUMENTS

| | | |
|---|---|---|
| CN | 101939268 | 1/2011 |
| CN | 102695684 | 9/2012 |
| EP | 405921 | 1/1991 |
| EP | 1884526 | 2/2008 |
| EP | 2093266 | 8/2009 |
| FR | 2924719 | 6/2009 |
| GB | 865380 | 4/1961 |
| WO | 93/15140 | 8/1993 |
| WO | 96/39364 | 12/1996 |
| WO | 99/39039 | 8/1999 |
| WO | 99/61538 | 12/1999 |
| WO | 02/02476 | 1/2002 |
| WO | 02/096819 | 12/2002 |
| WO | 2004/050978 | 6/2004 |
| WO | 2006120523 A1 | 11/2006 |
| WO | 2007/008412 | 1/2007 |
| WO | 2008/011455 | 1/2008 |
| WO | 2009/006532 | 1/2009 |
| WO | 2009/019232 | 2/2009 |
| WO | 2009/019235 | 2/2009 |
| WO | 2009/034549 | 3/2009 |
| WO | 2009/046521 | 4/2009 |
| WO | 2009/080696 | 7/2009 |
| WO | 2009/080938 | 7/2009 |
| WO | 2009/095617 | 8/2009 |
| WO | 2010/029266 | 3/2010 |
| WO | 2010/120748 | 10/2010 |
| WO | 2010/132641 | 11/2010 |
| WO | 2010/135637 | 11/2010 |
| WO | 2010139899 A1 | 12/2010 |
| WO | 2011/002730 | 1/2011 |
| WO | 2011/044490 | 4/2011 |
| WO | 2012/118939 | 9/2012 |
| WO | 2012/138723 | 10/2012 |

OTHER PUBLICATIONS

U.S. Appl. No. 14/487,152.*
SciFinder.com, CAS # 20018-09-1, "Diiomethyl-p-tolysulfone", Jan. 7, 2015.*
GE Power and Water, Spectrus NX1100 Fact Sheet, Jul. 2010.*
International Search Report, Application No. PCT/US/12/27226, Dated Jun. 25, 2012.
Written Opinion, Application No. PCT/US12/27226, Dated Jun. 25, 2012.
Arch Biocide Selection Guide, www.archbiocides.com.
PCT International Search Report and the Written Opinion, PCT/US2010/052028 filed Oct. 8, 2010, dated Feb. 11, 2011.
Response to the European Patent Office dated Feb. 3, 2006 for Serial No. 03768889.2.
Communication from the European Patent Office dated Oct. 6, 2005 regarding Serial No. 03768889.2.
Response to the European Patent Office dated Jul. 12, 2005 for Serial No. 03768889.2.
Communication from the European Patent Office dated Aug. 16, 2005 regarding Serial No. 03768889.2.
Declaration of Liang Chen signed May 9, 2013, 2 pgs.
Communication from the EPO dated May 20, 2010 regarding Opposition to EP Application No. 03768889.2 (EP Patent No. 1578879).
Communication from the EPO dated Oct. 15, 2007 regarding Opposition to EP Application No. 03768889.2 (EP Patent No. 1578879).
Correspondence to the EPO from the Opponent/Respondent regarding Opposition to EP Application No. 03768889.2 (EP Patent No. 1578879) dated Feb. 14, 2013 from Opponent.
Communication from the EPO dated Nov. 8, 2012 regarding Summons to attend Oral Proceedings regarding Opposition to EP Application No. 03768889.2 (EP Patent No. 1578879).
Communication from the EPO dated Oct. 31, 2012 regarding Preparation for Oral Proceedings—Instructions to Support Service regarding Opposition to EP Application No. 03768889.2 (EP Patent No. 1578879).
Correspondence to the EPO dated Oct. 19, 2012 from the Patentee responding to communication dated Jun. 19, 2012 regarding Opposition to EP Application No. 03768889.2 (EP Patent No. 1578879).
Correspondence to the EPO dated Oct. 18, 2012 from the Opponent/Respondent responding to communication dated Jun. 19, 2012 regarding Opposition to EP Application No. 03768889.2 (EP Patent No. 1578879).
Communication from the EPO dated Jun. 19, 2012 regarding Opposition to EP Application No. 03768889.2 (EP Patent No. 1578879).
Correspondence to the EPO dated Jun. 1, 2012 from the Patentee regarding Opposition to EP Application No. 03768889.2 (EP Patent No. 1578879).
Communication from the Boards of Appeal of the European Patent Office regarding Decision dated Apr. 5, 2012 regarding Opposition to EP Application No. 03768889.2 (EP Patent No. 1578879).
Communication from the EPO regarding Minutes of the Public Oral Proceedings before the Technical Board of Appeal regarding Opposition to EP Application No. 03768889.2 (EP Patent No. 1578879).
Correspondence to the EPO dated Apr. 3, 2012 from the Patentee regarding response to submission of Mar. 20, 2012 by the Opponent/Respondent regarding Opposition to EP Application No. 03768889.2 (EP Patent No. 1578879).
Communication from the EPO dated Mar. 23, 2012 confirming Oral Proceeding date regarding Opposition to EP Application No. 03768889.2 (EP Patent No. 1578879).
Correspondence to the EPO dated Mar. 20, 2012 from the Opponent/Respondent regarding Opposition to EP Application No. 03768889.2 (EP Patent No. 1578879).
Correspondence to the EPO dated Mar. 2, 2012 from the Patentee regarding Opposition to EP Application No. 03768889.2 (EP Patent No. 1578879).
Correspondence to the EPO dated Mar. 1, 2012 from the Opponent/Respondent regarding Opposition to EP Application No. 03768889.2 (EP Patent No. 1578879).
Communication from the EPO dated Dec. 21, 2011 regarding Summons to Oral Proceedings regarding Opposition to EP Application No. 03768889.2 (EP Patent No. 1578879).
Correspondence to the EPO dated Nov. 2, 2012 from the Opponent/Respondent regarding Opposition to EP Application No. 03768889.2 (EP Patent No. 1578879).
Communication from the EPO dated Aug. 11, 2010 regarding Opposition to EP Application No. 03768889.2 (EP Patent No. 1578879).
Communication from the EPO dated Jul. 27, 2010 regarding Opposition to EP Application No. 03768889.2 (EP Patent No. 1578879).

(56) References Cited

OTHER PUBLICATIONS

Correspondence to the EPO dated Jul. 21, 2010 from the Patentee regarding Opposition to EP Application No. 03768889.2 (EP Patent No. 1578879).
Communication from the EPO dated Mar. 19, 2010 regarding Opposition to EP Application No. 03768889.2 (EP Patent No. 1578879).
Communication from the EPO dated Mar. 19, 2010 regarding minutes of Oral Proceedings for Opposition to EP Application No. 03768889.2 (EP Patent No. 1578879).
Correspondence to EPO dated Jan. 22, 2010 from Opponent/Respondent regarding Opposition to EP Application No. 03768889.2 (EP Patent No. 1578879).
Correspondence to the EPO dated Jan. 11, 2010 from Opponent/Respondent regarding Opposition to EP Application No. 03768889.2 (EP Patent No. 1578879).
Correspondence to the EPO dated Jan. 11, 2010 from the Patentee regarding Opposition to EP Application No. 03768889.2 (EP Patent No. 1578879).
Correspondence to the EPO dated Jan. 7, 2010 from the Patentee regarding Opposition to EP Application No. 03768889.2 (EP Patent No. 1578879).
Communication from the EPO dated Jul. 14, 2009 regarding Summons to attend Oral Proceedings for Opposition to EP Application No. 03768889.2 (EP Patent No. 1578879).
Correspondence to the EPO dated May 6, 2008 from the Patentee regarding Opposition to EP Application No. 03768889.2 (EP Patent No. 1578879).
Correspondence to the EPO dated Feb. 11, 2008 from the Patentee regarding Opposition to EP Application No. 03768889.2 (EP Patent No. 1578879).
Communication from the EPO dated Nov. 16, 2007 regarding a Notice of Opposition filing for Opposition to EP Application No. 03768889.2 (EP Patent No. 1578879).
Communication from the EPO dated Oct. 19, 2007 regarding a Notice of Opposition filing for Opposition to EP Application No. 03768889.2 (EP Patent No. 1578879).
Correspondence from Opponent/Respondent to the EPO dated Oct. 15, 2007 regarding Opposition to EP Application No. 03768889.2 (EP Patent No. 1578879).
Office action from U.S. Appl. No. 13/037,725 dated Jul. 5, 2013.
Office action from U.S. Appl. No. 12/900,540 dated Jul. 5, 2013.
About.com "Monomeric Unit", accessed Jun. 18, 2012, http://composite.about.com/library/glossary/m/bldef-m3521.htm.
Blamire, John, "Science at a Distance", Science at a Distance, accessed Jun. 17, 2013, http://www.brooklyn.cuny.edu/bc/ahp/SDPS/SD.PS.polymers.html.
ChemSpider, D-Glucose, Jun. 18, 2013, 4 pages.
Filton, "Rapid Determination of Dextrose Equivalent by Cryoscopy", Oct. 22, 2006, Starch, vol. 31, issue 11, pp. 381-384.
International Search Report and Written Opinion from PCT/US10/34670 dated Oct. 28, 2010.
Alvatroni et al., "Maltodextrin molecular weight distribution influence on the glass transition temperature and viscosity in aqueous solutions", Carbohydrate Polymers, 58, pp. 323-334 (2004).
Dokic, et al., "Molecular characteristics of maltodextrins and rheological behaviour of diluted and concentrated solutions", Colloids and Surfaces, A: Physiocochemical and Engineering Aspects, 141, pp. 435-440 (1998).
Messina, M.J., "Legumes and soybeans: overview of their nutritional profiles and heath effects", Am. J. of clinical Nutrition, vol. 70, No. 3, pp. 439S-450S. Sep. 1999.
International Search Report and Written Opinion from PCT/US10/030852 dated Aug. 25, 2010.
International Search Report and Written Opinion from PCT/US10/040276 dated Oct. 1, 2010.
Office action from U.S. Appl. No. 12/758,910 dated Dec. 3, 2012.
Office action from U.S. Appl. No. 12/758,910 dated May 6, 2013.
Office action from U.S. Appl. No. 12/776,703 dated May 2, 2013.
Office action from U.S. Appl. No. 12/825,375 dated Oct. 9, 2012.
Office action from U.S. Appl. No. 12/900,540 dated Nov. 29, 2012.
Interview Summary from U.S. Appl. No. 12/900,540 dated Feb. 15, 2013.
Office action from U.S. Appl. No. 12/900,540 dated May 9, 2013.
Office action from U.S. Appl. No. 13/037,725 dated Oct. 15, 2012.
Office action from U.S. Appl. No. 13/037,725 dated May 6, 2013.
Office action from U.S. Appl. No. 13/187,650 dated May 3, 2013.
Handbook of Adhesive Technology: Chapter 15—Carbohydrate Polymers as Adhesives, by Melissa Baumann and Anthony Conner, edited by A. Pizzi and K. Mittal, New York: Marcel Dekker, Inc. 1994.
Archimica, "Vinylphosphonic acid and vinylphosphonic dimethyl ester", version 1, 2009.
Kim et al., "Characterization of Poly(styrene-b-vinylbenzylphosphonic acid) Copolymer by Titration and Thermal Analysis", Macromolecular Research, 2007, vol. 15. No. 6, pp. 587-594.
Signet Chemical, Glucidex Maltodextrin, Apr. 16, 2013.
"LX Stretch Hood Typical Values", Lachenmeier, retrieved from web at www.lachenmeier.com.
Office action from U.S. Appl. No. 12/825,375 dated May 23, 2013.
Office action from U.S. Appl. No. 12/825,375 dated Sep. 12, 2013.
Office action from U.S. Appl. No. 12/776,703 dated Aug. 15, 2013.
Office action from U.S. Appl. No. 12/900,540 dated Feb. 12, 2014.
Office action from U.S. Appl. No. 13/037,725 dated Feb. 12, 2014.
American Chemical Society, Citric Acid, Jan. 30, 2014, 3 pgs.
Kearsley, M. Physical and Chemical Properties of Glucose Syrups, Handbook of Starch Hydrolysis Products and their Derivatives, Chapman and Hall, 1995, 26 pgs.
Office action from European Application No. 10768139.7 dated Jan. 7, 2014, 4 pgs.
Office action from Chinese Application No. 201110401232.4 dated Jan. 30, 2014, 32 pgs.
Office action from U.S. Appl. No. 13/187,650 dated Nov. 26, 2013.
Office action from Chinese Application No. 201080051943.7 dated Mar. 3, 2014.
Office action from U.S. Appl. No. 12/776,703 dated Mar. 20, 2014.
Office action from U.S. Appl. No. 13/187,650 dated Mar. 7, 2014.
Office action from U.S. Appl. No. 12/825,375 dated Apr. 24, 2014.
Office action from Chinese Application No. 201080051943.7 dated Oct. 17, 2014.
Office action from Australian Application No. 2010303254 dated Oct. 10, 2014.
Office action from U.S. Appl. No. 12/776,703 dated Oct. 6, 2014.
Office action from U.S. Appl. No. 13/187,650 dated Nov. 6, 2014.
Office action from Chinese Application No. 201280018294.X dated Aug. 29, 2014.
Notice of Allowance from U.S. Appl. No. 12/900,540 dated Sep. 8, 2014.
Office action from U.S. Appl. No. 12/900,540 dated Jul. 15, 2014.
Office action from U.S. Appl. No. 13/234,336 dated Jul. 17, 2014.
Office action from U.S. Appl. No. 13/234,336 dated Jan. 14, 2015.
Office action from U.S. Appl. No. 12/825,375 dated Feb. 13, 2015.
Office action from European Application No. 15152030.1 dated Apr. 8, 2015.
Office action from Chinese Application No. 201110401232.4 dated Nov. 25, 2014.
Office action from U.S. Appl. No. 13/187,650 dated Mar. 20, 2015.
Office action from U.S. Appl. No. 14/302,604 dated Jan. 4, 2016.
Office action from U.S. Appl. No. 14/302,604 dated Jun. 29, 2015.
Office action from U.S. Appl. No. 13/234,336 dated May 4, 2015.
Office Communication from European Application No. 10768139.7 dated Apr. 7, 2015 received on Jun. 11, 2015.
Patent Examination Report from Australian Application No. 2010303254 dated May 8, 2015 received on Jun. 23, 2015.
Office action from Japanese Application No. 2013-556848 dated Jul. 8, 2015.
Office action from Chinese Application No. 201080051943.7 dated Jun. 30, 2015.
Communication from European Application No. 15152030.1 dated Aug. 3, 2015.
Office action from U.S. Appl. No. 12/825,375 dated Oct. 23, 2015.
Office action from U.S. Appl. No. 14/487,152 dated Oct. 26, 2015.

(56) References Cited

OTHER PUBLICATIONS

Notice of Allowance from U.S. Appl. No. 14/516,660 dated Nov. 6, 2015.
Office action from U.S. Appl. No. 13/234,336 dated Dec. 15, 2015.
Office action from U.S. Appl. No. 13/187,650 dated Nov. 16, 2015.
Office action from U.S. Appl. No. 14/516,660 dated May 15, 2015.
Office action from U.S. Appl. No. 12/825,375 dated Apr. 7, 2016.
Office action from U.S. Appl. No. 13/187,650 dated Mar. 28, 2016.
Office action from U.S. Appl. No. 13/187,650 dated Jul. 13, 2016.
Office action from U.S. Appl. No. 12/825,375 dated Dec. 1, 2016.
Office action from Canadian Application No. 2,777,078 dated Aug. 16, 2016.
Notice of Allowance from U.S. Appl. No. 14/487,152 dated Oct. 24, 2016.
Office action from U.S. Appl. No. 14/302,604 dated Nov. 3, 2016.
Chirife, J. et al, "A Simple Model for Predicting the Viscosity of Sugar and Oligosaccharide Solutions", J. of Food Engineering, 33, pp. 221-226 (1997).
de Meireless Brioude et al., "Synthesis and Characterization of Aliphatic Polyesters from Glycerol, by-Product of Biodiesel Production, and Adipic Acid", Materials Research, vol. 10, No. 4, 335-339 2007.
D. Pramanick et al., "Synthesis and biodegradation of copolyesters from citric acid and glycerol", Polymer Bulletin 19, pp. 365-370 (1988).
Ronald Alan Holser, "Thermal Analysis of Glycerol Citrate/Starch Blends", Journal of Applied Polymer Science, vol. 110, pp. 1498-1508 (2008).
Nagata et al., "Synthesis and enzymatic degradation of regular network aliphatic polyesters", Reactive & Functional Polymers 30 (1996) pp. 165-171.
Shi et al., "Characterization of citric acid/glycerol co-plasticized thermoplastic starch prepared by melt blending", Carbohydrate Polymers 69, pp. 748-755 (2007).
Pachauri et al., "Value-added Utilization of Crude Glycerol from Biodiesel Production: A Survey of Current Research Activities", An ASABE meeting Presentation, Portland, Oregon, Jul. 9-12, 2006, Paper No. 066223.
Volt et al., "Hyperbranched and Highly Branched Polymer Architectures—Synthetic Strategies and Major Characterization Aspects", Chem. Rev. 2009, 109, pp. 5924-5973.
Jan Trenkel-Amoroso, "Synthesis, Degradation and Practical Applications of Glycerol/Citric Acid Condensation Polymer", A Thesis submitted to Oregon State University, presented Dec. 9, 2008, 66 pgs.
Unal, "Synthesis and Characterization of Branched Macromolecules for High Performance Elastomers, Fibers, and Films, "Dissertation submitted to the Virginia Polytechnic Institute and State University, Nov. 16, 2005, 240 pages.
Reddy et al. "Wet Cross-Linking Gliadin Fibers with Citric Acid and a Quantitative Relationship between Cross-Linking Conditions and Mechanical Properties", J. Agric. Food Chem., vol. 57, No. 1, pp. 90-98, 2009.
Reddy et al., "Citric acid cross-linking of starch films", Food Chemistry, vol. 118, pp. 702-711, 2010.
Welch et al., "Curing Agents having low or zero phosphorus content for formaldehyde free DP Finishing with Polycarboxylic Acids", Textile Chemist and Colorist Journal, vol. 25, No. 10, Oct. 1993, pp. 25-29.
Clark M. Welch, "Formaldehyde-Free Durable Press Finishing", Surfactant Science Series, vol. 94, pp. 1-32, 2001.
International Search Report and Written Opinion from PCT/US12/32118 dated Sep. 11, 2012.
Office action from U.S. Appl. No. 14/110,079 dated Jan. 28, 2016.
Office action from U.S. Appl. No. 14/565,545 dated Apr. 22, 2016.
Office action from U.S. Appl. No. 14/565,545 dated Jul. 27, 2016.
Notice of Allowance from U.S. Appl. No. 14/487,152 dated May 6, 2016.
Office action from U.S. Appl. No. 14/302,604 dated Jul. 12, 2016.
Office action from U.S. Appl. No. 14/487,152 dated Jul. 14, 2016.
Office action from Japanese Application No. 2013-556848 dated May 31, 2016.
Supplemental Notice of Allowance from U.S. Appl. No. 14/487,152 dated Dec. 14, 2016.
Office action from U.S. Appl. No. 13/187,650 dated Jan. 25, 2017.

* cited by examiner

BIOCIDES FOR BIO-BASED BINDERS, FIBROUS INSULATION PRODUCTS AND WASH WATER SYSTEMS

CROSS REFERENCE TO RELATED APPLICATIONS

This application is continuation-in-part of U.S. patent application Ser. No. 12/900,540, filed Oct. 8, 2010, which claims priority to U.S. Provisional Patent Application Ser. No. 61/250,187 entitled "Bio-Based Binders For Insulation And Non-Woven Mats" filed Oct. 9, 2009; and a continuation-in-part of U.S. patent application Ser. No. 12/776,703, filed May 10, 2010, which claims priority to U.S. Provisional Patent Application Ser. No. 61/178,745 entitled "Bio-based Aqueous Binder For Fiberglass Insulation Materials And Non-Woven Mats With No Formaldehyde Added" filed May 15, 2009 all of which are expressly and wholly incorporated herein by reference.

BACKGROUND

The present invention relates generally to the processes for manufacture of fibrous insulation products, and more particularly, to biocides or biocidal agents useful for killing unwanted organisms associated with bio-based binders in manufacturing fiberglass insulation products.

Conventional fibers are useful in a variety of applications including reinforcements, textiles, and acoustical and thermal insulation materials. Although mineral fibers (e.g., glass fibers) are typically used in insulation products and non-woven mats, depending on the particular application, organic fibers such as polypropylene, polyester, and multi-component fibers may be used alone or in combination with mineral fibers in forming the insulation product or non-woven mat.

Fibrous glass insulation products generally comprise randomly-oriented glass fibers bonded together by a cured thermosetting polymeric material. Molten streams of glass are drawn into fibers of random lengths and blown into a forming chamber or hood where they are randomly deposited as a pack onto a moving conveyor or chain. The fibers, while in transit in the forming chamber and while still hot from the drawing operation, are sprayed with an aqueous dispersion or solution of binder. The residual heat from the glass fibers and from the flow of hot gases during the forming operation are sufficient to vaporize much of the water from the binder, thereby concentrating the binder dispersion and depositing binder on the fibers as a viscous liquid with high solids content. Sufficient binder is applied and cured so that the fibrous blanket can be compressed for packaging, storage and shipping, yet regains its thickness—a process known as "loft recovery"—when installed, e.g. in the insulation cavities of buildings. The binder composition also provides protection to the fibers from interfilament abrasion and promotes compatibility between the individual fibers.

The uncured fibrous pack is transferred to a curing oven where a gas, heated air for example, is blown through the pack to remove moisture, cure the binder and rigidly bond the glass fibers together in a three-dimensional structure known as a "blanket" with a desired thickness. After the binder has cured, the fiber insulation may be cut into lengths to form individual insulation products, and the insulation products may be packaged for shipping to customer locations. One typical insulation product produced is an insulation batt or blanket, which is suitable for use as wall insulation in residential dwellings or as insulation in the attic and floor insulation cavities in buildings. Another common insulation product is air-blown or loose-fill insulation, which is suitable for use as sidewall and attic insulation in residential and commercial buildings as well as in any hard-to-reach locations. Loose-fill insulation may be formed of small cubes that are cut from insulation blankets, compressed, and packaged in bags.

Historically, binders have been phenolic-formaldehyde resins, although more recently attempts have been made to reduce undesirable formaldehyde emissions from formaldehyde-based resins. Such approaches have included formaldehyde scavengers such as ammonia and urea, but these introduce other problems. In addition, some have focused on the use of polyacrylic acid with a polyhydroxyl crosslinking agent. See, for example, the polyacrylic acid/polyol/polyacid acid binder system described in U.S. Pat. Nos. 6,884,849 and 6,699,945 to Chen, et al.; and the binder chemistry disclosed in U.S. Pat. Nos. 7,258,802 and 7,780,858 to Miks.

In view of the existing problems with current binders, there remains a need in the art for a binder system that is not petroleum dependent, has no added formaldehyde, is bio-based and environmentally friendly, and is cost competitive.

SUMMARY OF THE INVENTION

In a first aspect, the invention relates generally to a method for controlling the growth of unwanted organisms in the process of manufacturing mineral fiber products said method comprising:

forming mineral fibers and applying to the fibers a bio-based binder having a nutrient that is an energy source; and adding to at least one of: raw ingredients used to prepare the bio-based binder; a bio-based binder composition; an aqueous dispersion of the bio-based binder; coolant water sprayed on mineral fibers; cleaning system water sprayed on forming equipment; washwater recovered from the cleaning system; washwater recovered from the forming operation; and finished mineral fiber product an effective amount of a biocide to kill at least one type of unwanted organism capable of using the nutrient as an energy source.

It will be observed that the effective amount of biocide may added prior to applying the bio-based binder to the mineral fibers, such as to the bio-based binder dispersion that is sprayed, to the composition that makes up the dispersion, or to raw ingredients of the binder composition. Alternatively, the effective amount of biocide may be added to coolant water sprayed on the mineral fibers, in which case it may end up in the washwater from the forming operation. The effective amount of biocide may also be added to cleaning water sprayed on the forming equipment, in which case it may end up in the washwater from the forming equipment. Finally, the effective amount of biocide may be added directly to washwater collected from the forming operation or forming equipment; via slip lines or directly to storage tanks. In the case of washwater, the biocide may be added with a frequency of every 2-3 days, or in response to organism load monitoring, e.g. by dip slide or other testing methods. In the washwater, biocide concentration may be within a range from about 0.01% to about 0.5% by weight, more likely from about 0.01% to about 0.1%.

The options of the above paragraph introduce several additional aspects of the invention. For example, in another aspect, the invention relates to an aqueous binder dispersion for use in the formation of fibrous mineral products, the binder dispersion comprising: at least one curable, bio-based binder including a nutrient that is an energy source; and an effective amount of a biocide to kill at least one type of unwanted organism capable of using the nutrient as an energy source. Such a binder dispersion may have an effective amount of biocide in the range of from about 0.005% to about 1% by weight.

In yet another aspect, the invention relates to a finished mineral fiber insulation product comprising: a plurality of randomly oriented mineral fibers; and a bio-based binder composition applied to at least a portion of said fibers, said binder composition including a nutrient that is an energy source; and an effective amount of a biocide to kill at least one type of organism capable of using the nutrient as an energy source. Such a finished product may have an effective amount of biocide in the range of from about 0.001% to about 2% by weight, more likely from about 0.01% to about 1%.

In the methods, the dispersion and finished product, the nutrient in the bio-based binder may be a carbohydrate having a dextrose equivalent number from 2 to 20, such as a starch, a maltodextrin or a pectin, or combinations thereof. The binder composition may further comprises a polycarboxylic crosslinking agent. Alternatively, the bio-based binder nutrient may comprise a bio-based protein mass.

In the methods, the dispersion and finished product, the biocide may be a pesticide or antimicrobial. If an antimicrobial, it may be an antibacterial, e.g. against anaerobic bacteria or aerobic bacteria or both; or it may be an antifungal, anti-mold, or any other antimicrobial.

BRIEF DESCRIPTION OF THE DRAWINGS

The advantages of this invention will be apparent upon consideration of the following detailed disclosure of the invention, especially when taken in conjunction with the accompanying drawings wherein.

DETAILED DESCRIPTION

Figure 1:
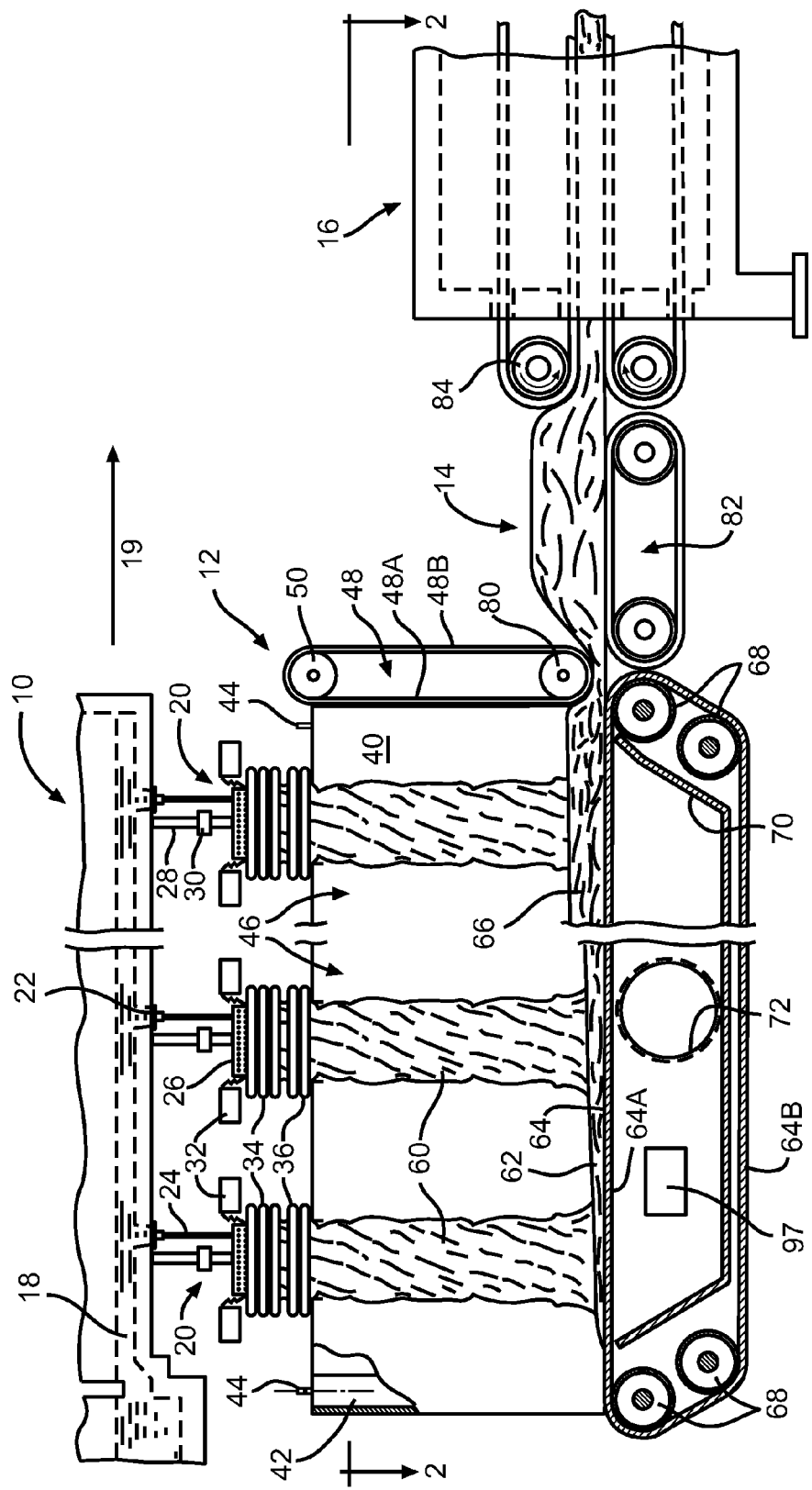
FIG. 1 is a partially sectioned side elevation view of a forming hood component of a manufacturing line for manufacturing fibrous products.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including books, journal articles, published U.S. or foreign patent applications, issued U.S. or foreign patents, and any other references, are each incorporated by reference in their entireties, including all data, tables, figures, and text presented in the cited references.

In the drawings, the thickness of the lines, layers, and regions may be exaggerated for clarity. It will be understood that when an element such as a layer, region, substrate, or panel is referred to as being "on" another element, it can be directly on the other element or intervening elements may also be present. Also, when an element is referred to as being "adjacent" to another element, the element may be directly adjacent to the other element or intervening elements may be present. The terms "top", "bottom", "side", and the like are used herein for the purpose of explanation only.

Unless otherwise indicated, all numbers expressing ranges of magnitudes, such as degrees or sheet speeds, quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements. All numerical ranges are understood to include all possible incremental sub-ranges within the outer boundaries of the range. Thus, a range of 30 to 90 degrees discloses, for example, 35 to 50 degrees, 45 to 85 degrees, and 40 to 80 degrees, etc.

The term "binder" and "binder composition"—even when modified by "natural" or bio-based"—refer to the binder chemicals or solids for a binder "dispersion." Binder "composition" may also include other ingredients and additives as described later. Binder "dispersion" refers to mixtures of binders or binder compositions in a medium or vehicle, typically water. Dispersions include true solutions, as well as colloids, emulsions or suspensions, and may have a relatively high, concentration, e.g. 20-40%, of binder solids or a lower concentration, e.g. 10%, of binder. References to "acidic binder" or "low pH binder" mean a binder having a dissociation constant (Ka) such that in an aqueous dispersion the pH is less than 7, generally less than about 6, and more typically less than about 4.

"Makeup water" refers to water added into the otherwise closed washwater recovery system from an external source that may include pond, river, lake, fresh, well, city or other source of water. Makeup water is generally clean and near neutral pH, that is, having a pH between about 6.5 and about 7.5 although in some cases the pH may be as low as about 6.0 or as high as about 9.5. Also in some cases makeup water may include washwater from other areas or systems.

"Mineral fibers" refers to any mineral material that can be melted to form molten mineral that can be drawn or attenuated into fibers. Glass is the most commonly used mineral fiber for fibrous insulation purposes and the ensuing description will refer primarily to glass fibers, but other useful mineral fibers include rock, slag and basalt.

General Fiber Forming Process

FIG. 1 illustrates many of the production components of a glass fiber insulation product manufacturing line including a forehearth 10, forming hood component or section 12, a ramp conveyor section 14 and a curing oven 16. Molten glass from a furnace (not shown) is led through a flow path or channel 18 to a plurality of fiberizing stations or units 20 that are arranged serially in a machine direction indicated by arrow 19 in FIG. 1. At each fiberizing station, holes or bushings 22 in the flow channel 18 allow a stream of molten glass 24 to flow into a spinner 26, which may optionally be heated by a burner (not shown). Fiberizing spinners 26 are rotated about a shaft 28 by motor 30 at high speeds such that the molten glass is forced to pass through tiny orifices in the circumferential sidewall of the spinners 26 to form primary fibers.

Blowers 32 direct a gas stream, typically air, in a substantially downward direction, turning them downward and attenuating them into secondary fibers that form a veil 60 that is forced downwardly. The glass fibers may have a diameter from about 2 to about 9 microns, or from about 3 to about 6 microns. The small diameter of the glass fibers helps to give the final insulation product a soft feel and flexibility. The fibers are generally distributed in a cross-machine direction by mechanical or pneumatic "lappers" (not shown), eventually forming a fibrous layer 62 on a porous conveyor 64 or chain. The layer 62 gains mass (and typically thickness) with the deposition of additional fiber from the serial fiberizing units, thus becoming a fibrous "pack" 66 as it travels in a machine direction 19 through the forming area 46.

One or more cooling rings 34 spray coolant liquid, such as water, on veil 60 to cool the forming area and, in particular, the fibers within the veil. Other coolant sprayer configurations are possible, of course, but rings have the advantage of delivering coolant liquid to fibers throughout the veil 60 from a multitude of directions and angles. A binder dispensing system includes binder dispersion sprayers 36 to spray binder dispersion onto the veil 60. Illustrative coolant spray rings and binder spray rings are disclosed in US Patent Publication 2008-0156041 A1, to Cooper, and in co-pending provisional application 61/421,306 filed Dec. 9, 2010, both incorporated herein by reference. FIG. 1 depicts three fiberizing units 20, but any number may be used. For insulation products, typically from two to about 15 units may be used in one forming hood component for one line. Binders are discussed in more detail below.

Figure 2:
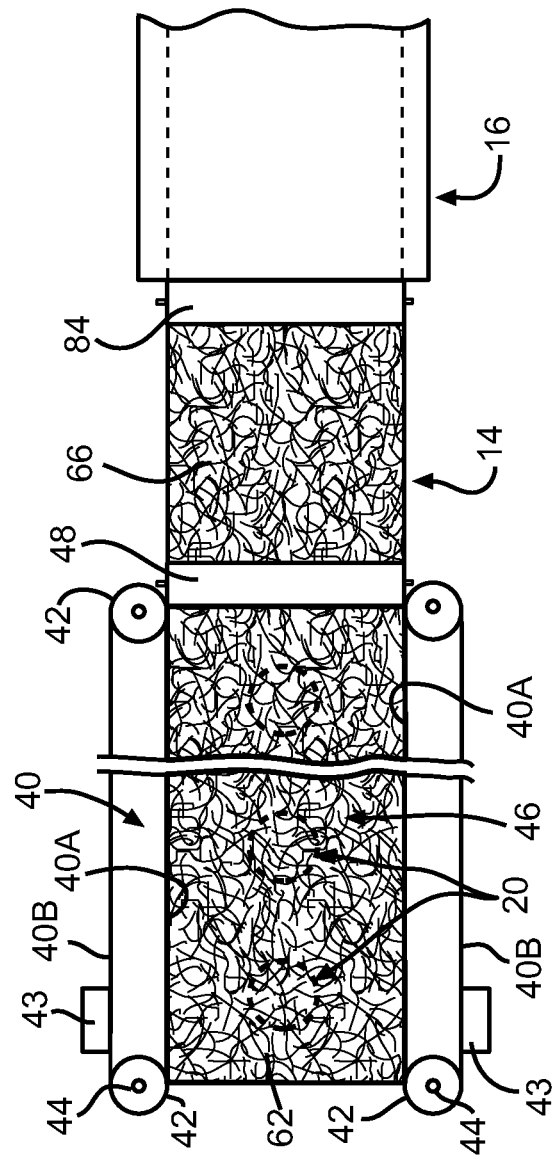
FIG. 2 is a partially sectioned top view taken along line 2-2 of FIG. 1.

As shown in FIGS. 1 and 2, the forming hood section or component 12 is further defined by at least one hood wall 40, and usually two such hood walls on opposing sides of the conveyor 64 to define a forming chamber or area 46. For clarity in FIG. 1, the hood wall 40 is depicted on only one side (behind conveyor 64), and a portion of the wall 40 on the left end is removed to reveal a roller 42 and its axis 44. Typically, each of the hood walls 40 takes the form of a loop or belt having two flights 40A and 40B (see FIG. 2). Inward facing flight 40A defines a sidewall of the forming area 46 and moves through the forming area by rotating about vertical rollers 42; while outside flight 40B closes the loop outside of the forming area 46. End walls 48 (one shown at the right end of the forming area 46) of similar belt construction may further enclose the forming area 46 with an inward facing flight 48A and an outward return flight 48B. As shown in FIGS. 1 and 2, however, the rollers 50, 80 for the end wall 48 may be oriented transversely compared to the rollers 42. A similar end wall (not shown) may be present on the left end of the forming area 46.

"Production components" include "forming hood components" 102 (FIG. 3) means at least one hood wall, more typically including two side hoodwalls 40 and optional end walls 48, that define the fibrous pack forming area 46 above the conveyor 64 and below the fiberizing units 20. The terms "forming hoodwall", "hoodwall" and "hood wall" may be used interchangeably herein. While most of the binder sprayed into the forming area ends up in the fibrous pack, it has been found that as much as about 90% of the binder that does not remain in the pack accumulates instead on the hoodwalls. Only a minor portion (e.g. less than about 10% of the binder that does not remain in the pack) passes through to reach the conveyor 64, or other downstream components.

"Production components" also include the "downstream air components" 92 which have the primary purpose of creating and maintaining a negative pressure below the chain or conveyor 64 in order to draw through the air injected to the forming area 46 by blowers 32. The "downstream air components" 92 thus include the air handling system downstream from the conveyor 64, including the conveyor 64 itself. Note that "downstream" here refers to the direction of airflow, not the machine direction 19. Conveyor 64 is porous and may also include two flights 64A and 64B. Upper flight 64A travels in the machine direction 19, revolves about one or more rollers 68 to lower flight 64B which revolves about further rollers 68 to complete the belt. Beneath the upper flight 64A of conveyor chain 64, one or more suction boxes 70 are connected via duct 72 to a particle separator (not shown) that decelerates the air flow to allow particulates to fall and separate from the air stream, such as drop-out boxes, cyclonic separators, de-misters and the like. Further downstream, a forming fan or blower and its housing (neither shown) ultimately provide the negative pressure in the suction box 70 that aids in removing air entering the forming area 46 to reduce turbulence. A final portion of the downstream air components 92 includes further ductwork leading ultimately to a discharge stack (not shown). In spite of the negative pressure provided by the downstream air components 92, the airflow and turbulence caused by the blowers 32 frequently cause binder from sprayers 36 and glass fibers from the veil 60 to become adhered to the hood walls 40, 48 as described above.

Still referring to FIGS. 1 and 2, the uncured pack 66 exits the forming hood area 46 under roller 80 and, in the absence of the downward influence of the blowers 32 and the suction box 70, (optionally aided by a pack lift fan, not shown) the uncured pack 66 immediately regains a certain degree of loft or height ("ramp height") as it travels along the conveyor 82 toward the curing oven 16. Spaced-apart rollers or porous conveyors 84 force the pack 66 down to a desired thickness (or "bridge height") and the product is cured at this thickness in the oven 16.

The curing oven 16 may be operated at a temperature from about 100° C. to about 325° C., or from about 250° C. to about 300° C. The insulation pack 66 may remain within the oven 16 for a period of time sufficient to crosslink (cure) the binder and form the insulation blanket. The bio-based binder compositions cure at a temperature that is lower than the curing temperature of conventional formaldehyde binders. This lower curing temperature requires less energy to heat the insulation pack, which results in lower manufacturing costs. The emerging cured product, or "blanket", then continues to cutting and packaging steps.

In one exemplary embodiment, the binder is used to form an insulation product. Fibrous insulation products are generally formed of randomly oriented inorganic fibers bonded together by a cured thermoset polymeric material. Examples of suitable inorganic fibers include glass fibers, wool glass fibers, and ceramic fibers. Optionally, other reinforcing fibers such as natural fibers and/or synthetic fibers such as polyester, polyethylene, polyethylene terephthalate, polypropylene, polyamide, aramid, and/or polyaramid fibers may be present in the insulation product in addition to the glass fibers.

The term "natural fiber" as used in conjunction with the present invention refers to plant fibers extracted from any part of a plant, including, but not limited to, the stem, seeds, leaves, roots, or phloem. Examples of natural fibers suitable for use as the reinforcing fiber material include basalt, cotton, jute, bamboo, ramie, bagasse, hemp, coir, linen, kenaf, sisal, flax, henequen, and combinations thereof. Insulation products may be formed entirely of one type of fiber, or they may be formed of a combination of types of fibers. For example, the insulation product may be formed of combinations of various types of glass fibers or various combinations of different inorganic fibers and/or natural fibers depending on the desired application for the insulation. The embodiments described herein are with reference to insulation products formed entirely of glass fibers.

Wash/Process Water Storage and Re-Cycling

A hoodwall cleaning system 43, typically comprising a wiper or scraper blade and a sprayer or dispenser is disposed along a leading edge of the outside flights 40B and 48B. A source of washing water is fed to the cleaning system 43 and the sprayer sprays water on the outside flight 40B of the hoodwall, thus aiding the scraper to remove debris (e.g. binder and glass fibers) that has accumulated on the hoodwall 40. The exact configuration of the cleaning system 43 is not critical.

The belt construction of the forming hood walls 40, 48 facilitates the ability to clean them separately from other downstream air components. While not essential to the present invention, it has been found to be advantageous in systems with acidic binders to maintain two separate wash systems. Since the acid is highly corrosive, if it can be somewhat segregated to the "forming hood components" 102 where it is used, then a separate alkaline wash system can be used to protect other components, such as "downstream air components" 92, without causing mixing and neutralization of the acids and bases. The alkaline wash of downstream air components 92 reduces the corrosive effect of acidic binder than finds it way downstream, and preserves the production equipment. Details of such an optional, segregated wash systems are described in the patent literature, including for example, U.S. Pat. No. 7,754,020 to Cline, et al., incorporated herein by reference.

Figure 3:
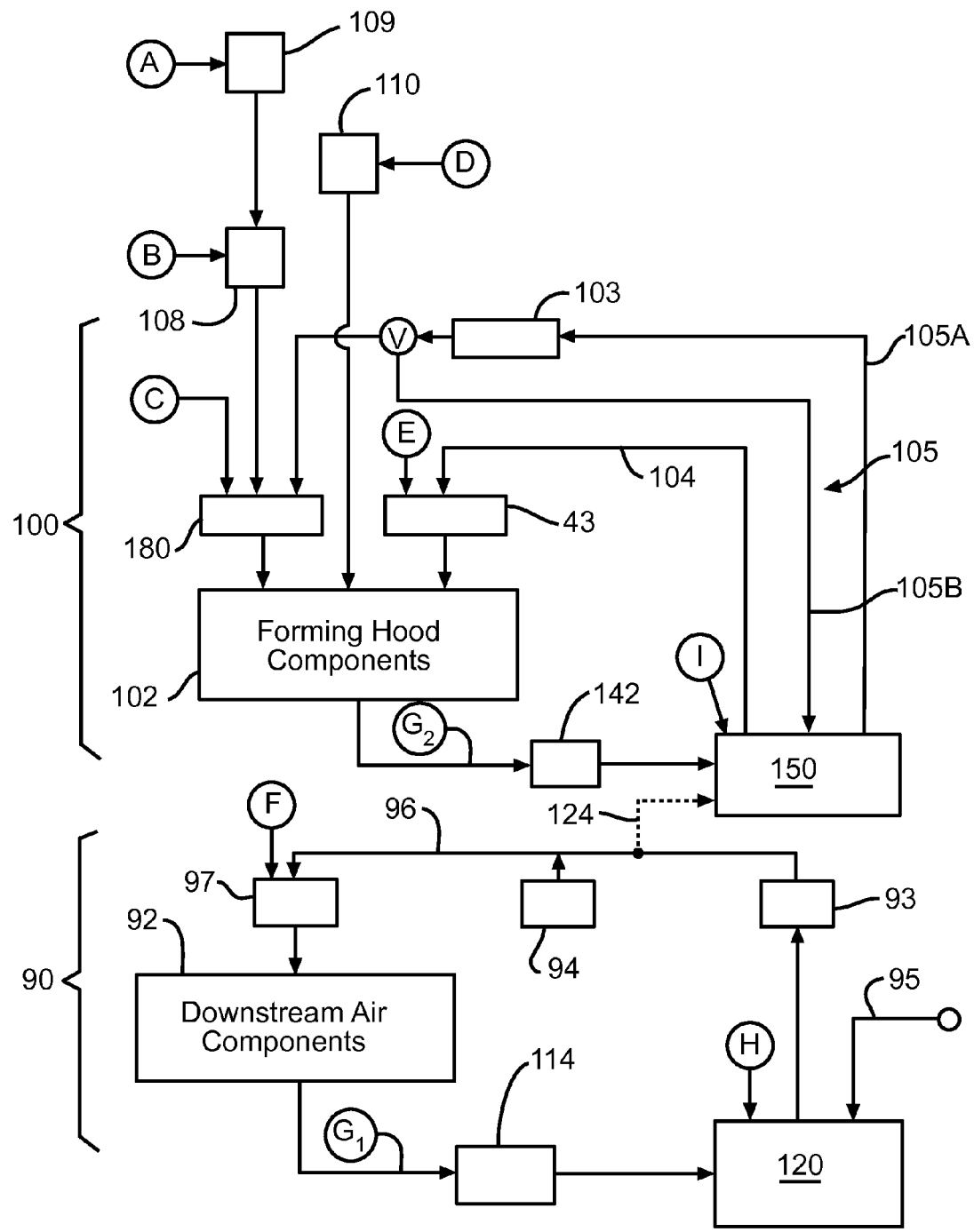
FIG. 3 is a simplified schematic diagram showing distinct recovery loop systems for a bulk washwater recovery system and a hoodwall washwater recovery system.

FIG. 3 represents a schematic diagram for a washwater control system that minimizes corrosion and reduces acidic waste by recycling waste washwater in separate, distinct recovery loops. The system thus comprises a first or "bulk" washwater recovery loop 90 that is used for the "downstream air components" 92 and a second or "hoodwall" washwater recovery loop 100 that is used for the forming hood components 102. It is desirable to segregate these washwater systems since it is preferable to use high pH washwater on the "downstream air components" 92 to reduce the effect of acidic corrosion, yet it is desirable to maintain the acidity of the binder dispersion for reuse in the forming hood, e.g. for mixing up new batches of binder dispersions.

In the "bulk" washwater recovery loop 90, waste washwater is screened or filtered at 114 to remove glass fibers, collected in bulk washwater supply tank 120. Additional makeup water may be added at 95 to maintain the level in supply tank 120. From supply tank 120, bulk washwater is re-circulated via line 96 back to bulk cleaning system 97 for spraying and washing of downstream air components 92 to complete the recovery loop. Within the loop, pH may be measured at sensor 93 and if the pH is at or below a predetermined target set point, a base such as sodium hydroxide may be added at 94 before the washwater is returned to the bulk cleaning system 97. Maintaining an alkaline bulk washwater minimizes the corrosive effect of any low pH binder that does reach downstream air components 92.

In the "hoodwall" washwater recovery loop 100, waste washwater from the hoodwall is filtered at 142 and collected as filtered hoodwall washwater (FWS) in a binder reclaim tank 150. To replenish the level in the binder reclaim tank 150, water may be added from an alternate source such as makeup water or bulk washwater that may be diverted via cross-system line 124. From binder reclaim tank 150, the FWS may have dual uses upon re-cycling to the forming hood. First, FWS may be used for further hoodwall washing, shown by path 104 leading to a hoodwall cleaning system 43. Second, FWS may be used to prepare new binder dispersion in binder dispersion tank 180, shown by re-circulating loop path 105 with diverter valve 156.

Natural Binder Compositions

"Binders" are well known in the industry to refer to thermosetting organic agents or chemicals, often polymeric resins, used to adhere glass fibers to one another in a three-dimensional structure that is compressible and yet regains its loft when compression is removed. Phenolic/formaldehyde binders have been used in the past. While the formaldehyde provided a natural biocidal activity, it has also been associated with environmental concerns. Some manufacturers have attempted to use formaldehyde-free binder systems. Two main approaches to formaldehyde-free binder systems have been developed. First, there are the polyacrylic acid and polyol polymers. An example is the polyacrylic acid/polyol/polyacid acid binder system described in U.S. Pat. Nos. 6,884,849 and 6,699,945 to Chen, et al.

A second category of formaldehyde-free binders are referred to as "bio-based" or "natural" binders. "Bio-based binder" and "natural binder" are used interchangeably herein to refer to binders made from nutrient compounds, such as carbohydrates, proteins or fats. Because they are made from nutrient compounds they are very environmentally friendly. However, they are also friendly as growth media for unwanted organisms as described herein. Unless context indicates otherwise (such as in the preceding paragraph), references in this application to binders, binder compositions or binder dispersions are referring to natural or bio-based binders.

Carbohydrate Binder Compositions

Natural binders may be made from carbohydrates, including starches, pectins, dextrins, maltodextrins or other polysaccharides of varying length) coupled with polyfunctional carboxylic acids like citric acid. Exemplary carbohydrate based binder compositions are disclosed in commonly owned U.S. patent application Ser. No. 12/900,540, filed Oct. 8, 2010, and incorporated herein by reference. In one or more exemplary embodiments, the binder includes at least one carbohydrate that is natural in origin and derived from renewable resources. For instance, the carbohydrate may be derived from plant sources such as legumes, maize, corn, waxy corn, sugar cane, milo, white milo, potatoes, sweet potatoes, tapioca, rice, waxy rice, peas, sago, wheat, oat, barley, rye, amaranth, and/or cassava, as well as other plants that have a high starch content. The carbohydrate polymer may also be derived from crude starch-containing products derived from plants that contain residues of proteins, polypeptides, lipids, and low molecular weight carbohydrates. The carbohydrate may be selected from monosaccharides (e.g., xylose, glucose, and fructose), disaccharides (e.g., sucrose, maltose, and lactose), oligosaccharides (e.g., glucose syrup and fructose syrup), and polysaccharides and water-soluble polysaccharides (e.g., pectin, dextrin, maltodextrin, starch, modified starch, and starch derivatives).

The carbohydrate polymer may have a number average molecular weight from about 1,000 to about 8,000. Additionally, the carbohydrate polymer may have a dextrose equivalent (DE) number from 2 to 20, from 7 to 11, or from 9 to 14. The carbohydrates beneficially have a low viscosity and cure at moderate temperatures (e.g., 80-250° C.) alone or with additives. The low viscosity enables the carbohydrate to be utilized in a binder composition. In exemplary embodiments, the viscosity of the carbohydrate may be lower than 500 cps at 50% concentration and between 20 and 30° C. The use of a carbohydrate in the inventive binder composition is advantageous in that carbohydrates are readily available or easily obtainable and are low in cost.

In addition, the binder composition contains a crosslinking agent. The crosslinking agent may be any compound suitable for crosslinking the carbohydrate. In exemplary embodiments, the crosslinking agent has a number average molecular weight greater than 90, from about 90 to about 10,000, or from about 190 to about 4,000. In some exemplary embodiments, the crosslinking agent has a number average molecular weight less than about 1000. Non-limiting examples of suitable crosslinking agents include polycarboxylic acids (and salts thereof), anhydrides, monomeric and polymeric polycarboxylic acid with anhydride (i.e., mixed anhydrides), citric acid (and salts thereof, such as ammonium citrate), 1,2,3,4-butane tetracarboxylic acid, adipic acid (and salts thereof), polyacrylic acid (and salts thereof), and polyacrylic acid based resins such as QXRP 1734 and Acumer 9932, ("Acumer") both commercially available from The Dow Chemical Company. In exemplary embodiments, the crosslinking agent may be any monomeric or polymeric polycarboxylic acid, citric acid, and their corresponding salts. The crosslinking agent may be present in the binder composition in an amount up to about 50% by weight of the binder composition. In exemplary embodiments, the crosslinking agent may be present in the binder composition in an amount from about 5.0% to about 40% by weight of the total solids in the binder composition or from about 10% to about 30% by weight. Other potential agents and additives that may be present in the binder composition are described below.

Non-Carbohydrate Binder Compositions

An alternative to the carbohydrate bio-based binder composition is a protein bio-based binder composition such as those described in U.S. patent application Ser. No. 12/776,703, filed May 10, 2010, and incorporated herein by reference. Such a binder includes a protein-containing biomass and a pH adjuster, and optionally, a crosslinking agent and/or a moisture resistant agent.

In exemplary embodiments, the binder composition includes at least one protein-containing biomass that is natural in origin and derived from renewable resources. For instance, the protein may be derived from plant sources, principally from legumes and nuts, or from animal sources. Well-known legumes include alfalfa, clover, peas, beans, lentils, lupins, mesquite, carob, soy, and peanuts. Of these, peas, beans, soy and peanuts are excellent source of protein. (See e.g. M. J. Messina, "Legumes and soybeans: overview of their nutritional profiles and health effects" in American Journal of Clinical Nutrition, Vol. 70, No. 3, 439S-450S, September 1999, incorporated by reference.) Specific beans high in protein include black, red, lima, chickpea, kidney, lentil, navy, mung, soy, pinto, and great northern. Other high protein plant sources include walnuts and peanuts. Alternatively, the protein may come from animal sources such as, but not limited to, eggs, blood, meat, and fish. In some exemplary embodiments, the protein-containing biomass contains up to about 95% protein, and in other exemplary embodiments, up to 50, 75 or 90% protein. The protein-containing biomass may be present in the binder composition in an amount from about 25% to about 99% by weight of the binder composition, or from about 50% to about 95% by weight.

Additionally, the protein bio-based binder composition contains a pH adjuster in an amount sufficient to adjust the pH to a desired level. The pH may be adjusted depending on the intended application, or to facilitate the compatibility of the ingredients of the size composition. In exemplary embodiments, the pH adjuster is utilized to adjust the pH of the binder dispersion to an acidic pH. Examples of suitable acidic pH adjusters include mono- or polycarboxylic acids, such as, but not limited to, citric acid, acetic acid, and sulfuric acid, anhydrides thereof, and inorganic salts that can be acid precursors. The acid adjusts the pH, and in some instances, acts as a crosslinking agent. The pH of the binder dispersion, when in an acidic state, may range from about 1 to about 6, and in some exemplary embodiments, from about 1 to about 5. In at least one exemplary embodiment, the pH of the binder dispersion is about 1. The pH adjuster in an acidic binder composition may be present in the binder composition in an amount from about 3.0% to about 20% by weight of the binder composition, or from about 5.0% to about 15% by weight.

In addition, the protein bio-based binder composition may contain a crosslinking agent, such as phenols (e.g., tannic acid), resorcinol, polyamines, polyimines, glyoxal, glutardialdehyde, malose, dicarboxylic acid, esters of dicarboxylic acid, polycarboxylic acid, and combinations thereof. The crosslinking agent may be present in the binder composition in an amount up to about 20.0% by weight of the binder composition. In exemplary embodiments, the crosslinking agent may be present in the binder composition in an amount from about 5.0 to about 20.0% by weight of the binder composition, or from about 7.0 to about 15.0% by weight. Other potential agents and additives that may be present in the binder composition are described below.

Finally, it is envisioned that bio-based binder compositions may be produced from nutrient oils, fats, waxes and other hydrocarbon-based compounds that are not classified as carbohydrate or protein. Since such nutrients may provide a source of energy that supports organism growth, they are included within the bio-based binders described herein.

Additives to Binder Compositions

In each of the carbohydrate and non-carbohydrate classes of binder compositions, other additives and agents may be present in the composition, each at its known or typical effective level. For example, catalysts (e.g. typically an alkalai metal salt of a phosphorous-containing acid, such as sodium hypophosphite, sodium phosphate, potassium phosphate, disodium pyrophosphate); silanes or other coupling agents; process aids for enhanced pack formation, such as polyols, viscosity modifiers, surfactants, defoaming agents, dust reducers, and lubricants; corrosion inhibitors; buffers; crosslinking density enhancers or facilitators; moisture resistance agent; extenders; and additives like dyes, pigments, colorants, UV stabilizers, emulsifiers, preservatives and the like, all may also be present. Additives may or may not also serve as a nutrient base for organism growth. If they are a nutrient base, such as vegetable oils in current use as de-dusters emulsions in binder dispersions, they may also benefit from the incorporation of biocides.

In accordance with one embodiment of the invention, the binder compositions will contain a biocide as described below.

Biocidal Agents

The presence of the nutrient used in the binder composition, along with water, dust and other potential carbon sources, may support the growth and proliferation of organisms. Such organisms may be classified in many ways. For example, some organisms may be "wanted" (e.g. probiotics in nutritional products) while others are "unwanted" for a variety of reasons, such as they cause disease, produce toxins, or are otherwise pathogenic, or simply because they cause malodorous fragrance, discoloration, and/or deterioration of the binder composition, insulation product, or washwater.

Organisms may also be classified on a taxonomical basis, which separates bacteria, fungi, molds, insects, nematodes, yeasts, algae, protozoa, etc. into distinct groups. Biocides may be classified on a similar basis. According to one source, biocides fall into two main groups: (1) pesticides, which include fungicides, herbicides, insecticides, algicides, molluscicides, miticides, nematodicides, and rodenticides; and (2) antimicrobials, which include germicides, antibiotics, antibacterials, antivirals, antifungals, antimycotics, anti-mold agents, yeasticides, antiprotozoals and antiparasites. Organisms and biocides may also be classified based on their preference for a particular habitat medium (e.g. in an acidic binder dispersion, or an insulation batt or a washwater reservoir); or on myriad other bases.

Bacteria found in the washwater may include aerobic and anaerobic bacteria. Anaerobic bacteria, the more harmful of the two, thrive in anaerobic (little or no oxygen) habitat media, and include the sulfate-reducing bacteria. They must have anaerobic conditions which may be found in micro-environments such as small anaerobic pockets under deposits or in accumulated debris in otherwise aerobic washwater. They use sulfate as their last electron acceptor and convert it to hydrogen sulfide, a material notorious for its corrosivity to virtually all metals. The production of hydrogen sulfide and resulting corrosion is particularly harmful to process piping and equipment, as well as producing an unpleasant odor. This is especially true if the washwater is stored for some period of time before reuse. This can cause health problems for plant personnel and others who come into contact with the organisms. While not as harmful as anaerobic bacteria, aerobic bacteria (live in the presence of oxygen) may nonetheless cause health problems for those plant personnel that come into contact with it, as well as cause some corrosion and blockage of process piping and equipment. For example, *Legionella* can grow in the storage tanks and reservoirs. Other unwanted bacteria of interest include: *E. Coli, Pseudomonas, Cryptosporidium, Campylobacter, Salmonella, Staphylococcus* (especially methicillin resistant strains, MRSA) and others. While bacteria are among the most common and most harmful organisms that form in washwater, other unwanted organisms may also form and cause various problems.

"Biocides" or "biocidal agents" may be used interchangeably herein to refer to agents that reduce, kill or suppress the growth of unwanted organisms, regardless of their taxonomic or other classification. Biocides may also be organized in multiple ways: e.g. based on chemical composition similarities; potency; taxonomic group against which they are active (e.g. bacteriocidal or fungicidal); or on the basis of many other properties.

The amounts and types of organisms that grow in the washwater or other systems in turn depend on a variety of factors. For example, the type of binder used in the process and the amount of time the water is stored before being reused affect the amounts and types of organisms that grow. Other factors that contribute to an organism's growth will be apparent to those skilled in the art. The amount of biocide that must be added to be effective in practicing the invention depends on the amounts and types of organisms that grow in the system, and on the volume of the system being treated. Thus, the effective amount is determined empirically for each biocide, for each organism in each system. For purposes of the invention, an effective amount is defined as that concentration of biocide required to maintain the growth of unwanted organisms at or below a maximum level that might pose a health or safety risk or other unpleasant condition. In general for bacteria, this maximum level is about $10^4$ CFU/ml, preferably less than about $10^3$ or $10^2$ CFU/ml. For mold and other organisms, the maximum desirable levels may be determined by comparison against standards, such as is done in Example 2. Biocide concentration ranges thought to be "effective" in general, without regard to specific organism or biocide, are provided in Table B, below for various systems.

Chemical Categorization

As noted, the bio-based binder composition may also contain one or more biocide. Biocides fall into many chemical classes, including, for example, quaternary ammonium salts, halogens such as iodine, bromine and chlorine, and isothiazoline derivatives, to name a few. Table A, below identifies some biocides by chemical class or mechanism, as well as listing some specific representative compounds from each class, and the type of organism against which they are typically used as biocides. It is to be appreciated that combinations of agents may be employed, and some suppliers of brand name biocides include more than one agent in a branded product. It may be desirable to select combination agents having different activity spectra.

TABLE A

Typical Biocides by Class

| Class | Illustrative compounds (italics indicate a supplier; quotation marks indicate a "tradename") | Typical Activity |
| --- | --- | --- |
| chlorines | hypochlorous acid (HOCl); triazinetrione (dichlor); trichloro-s-triazinetrione, (trichlor); magnesium chloride; sodium hypochlorite | general biocide killing germs, micro-organisms, algae, etc. |
| bromines | 2-bromo-2-nitropropane-1,3-diol (BNP); dibromoacetonitrile; 2,2-dibromo-3-nitrilopropionamide; sodium bromide (*Houghton*); Sulfamic acid, N-Bromo, sodium salt | Bacteria, yeast, molds |
| iodines | 3-iodo-2propyl-n-butylcarbamate; 3-Iodo-2-Propynyl Butylcarbamate (IPBC); diiodomethyl-p-tolysulfone; | Fungi, yeast, molds |

TABLE A-continued

Typical Biocides by Class

| Class | Illustrative compounds (italics indicate a supplier; quotation marks indicate a "tradename") | Typical Activity |
|---|---|---|
| Other halogens | halogenated hydantoins | |
| isothiazoline derivatives | 5-chloro-2-methyl-4-isothiazolin-3-one (e.g. "T-360", "Kathon"); 1,2-Benzisothiazolin-3-one (BIT); | Fungi, algae, bacteria |
| | N-butyl-1,2-benzisothiazolin-3-one (BBIT); Dichloro-2-n-octyl-4-isothiazolin-3-one (*Dow*) | Bacterial, yeast, mold |
| quaternary ammonium compounds | Benzalkonium chloride | algae |
| Misc. other | Poly (hexamethylene biguanide) hydrochloride (PHMB); | Fungi, yeast, molds, bacteria & algae |
| | Glutaraldehyde (*Arch*); | Bacteria, yeast, molds |
| nitrates | magnesium nitrate | |
| metals | Silver; copper | Bacteria, mold |
| | Zinc pyrithione (*Arch*); | |
| ozone | ozone | Bacteria, mold |
| radiation | ultraviolet radiation | Bacteria, mold |

The biocide or combination of biocides used to treat the washwater system should be effective against both anaerobic and aerobic bacteria, and particularly against harmful sulfate-reducing bacteria. A commonly used biocide is sodium bromide; which is most effective when mixed in water and activated by a chlorine source (such as chlorine or sodium hypochlorite). Sodium bromide effectively kills both types of bacteria. Thus, it is a commonly used biocide for this type of water treatment. Another particular biocide that has been found useful in washwater treatments is "T-360," an isothiazolin class biocide (CAS 26172554; 5-chloro-2-methyl-4-isothiazolin-3-one) available from PMC Water Systems Service, Ontario, as a liquid in concentrations from about 1% to about 5%. Usage is in the range that produces the target concentration or controls organism growth to desired amounts. In one embodiment, about one gallon of 5% T-360 is added every other day to a washwater system of about 40,000 gallons.

T-360 and sodium bromide are just two examples of suitable biocides for treating the washwater. Any effective biocide may be used, and any substance that effectively reduces nutrients available to organisms in the washwater without otherwise harming or hampering the process may be used. An effective biocide should kill or inhibit the growth of harmful aerobic and anaerobic bacteria. Further, it should not alter the composition of the binder, corrode process piping or equipment, or cause blockage in the process piping.

In addition to the use of chemical biocides, other methods can be used to treat the washwater. For example, the washwater can be exposed to radiation at sufficient intensity to kill organisms present in the water. Of the numerous radiation treatments known to those skilled in the art, ultraviolet radiation is preferred.

Use in Systems

Since the unwanted organisms may survive on the nutrients of a bio-based binder, the presence of unwanted organisms may develop anywhere that bio-based binders or their ingredients or by-products occur. In particular, five areas are primary targets: the raw ingredients (dry or wet), the bio-based binder compositions themselves (dry or wet), bio-based binder dispersions (wet), washwater collected from the forming and/or cleaning process (wet), and the ultimate fibrous product (dry). Consequently, any of these locations are potential targets for biocide use, particularly those where a nutrient source is stored for any length of time. A biocide may be introduced into the system(s) in several ways, via several locations.

FIG. 3, described above with respect to washwater recovery loops 90, 100, also illustrates many of these locations and potential biocide input routes. The process starts with receipt or manufacture of the raw ingredient nutrient materials 109. Sources of nutrient carbohydrates and proteins are described above. These, along with cross-linking agent, catalysts and other additives are combined to form binder compositions 108. Biocides may be desired in the raw ingredients (e.g. input A) and/or in the binder compositions (input B). Some ingredients of a binder composition may not be added until the liquid binder dispersion is prepared in binder dispersion tank 180. Biocide may alternatively or additionally be included as part of the liquid binder dispersion (input C). Binder is sprayed onto the glass fibers in the forming hood, as discussed above, and thus finds its way into finished product and into the hoodwall washwater. For this reason, it is efficient to add biocide to binder, since it reaches so many of the locations where biocide may be desired.

Other routes are useful for ultimately reaching the washwaters indirectly, as illustrated in FIG. 3. First, coolant liquid 110 is generally sprayed into the forming hood to cool the fibers and hot environment. Excess that is neither evaporated in the forming hood nor captured in the pack ends up in the hoodwall washwater, so biocide may be input at D to the coolant liquid 110 as a means to reach washwater. In addition, cleaning and/or rinsing liquids are sprayed on or applied to forming hood components and equipment by cleaning system 43 and these are typically captured in the washwater, so biocide may be input at E to the cleaning solutions. Similarly, cleaning and/or rinsing liquids are sprayed on or applied to downstream air components or equipment by cleaning system 97 and these are typically captured in the bulk washwater, so biocide may be input at F to the cleaning solutions.

A biocide may be input directly into the resultant washwater via the conduits (represented generally as G1, G2) or into the storage systems 120, 150 (as represented by inputs H, I). As previously noted, the separate hoodwall and bulk washwater systems 90, 100 described above are not essential to the present invention, but may represent a preferred arrangement. A potential method is to pump or otherwise inject a biocide in liquid form into a slip stream taken off the main washwater recycle loop. The slip stream is then sent back into the main recycle stream before being sent to a washwater reservoir. A metering pump may be used to automatically control the amount of biocide injected into the slip stream depending on system needs. Alternatively, dip slide or other sample testing of the wash water may take place periodically, and in response to the result of that testing, a bolus of biocide may be added from a storage drum (not shown) to the washwater storage tank 120, 150 to achieve suitable effective concentrations and appropriate organism loads.

Finally, while use of a biocide in a binder is an efficient means to protect finished products, a biocide may also be added directly to the final fibrous mineral product itself. This may be done by spraying the product with biocide, which typically would be done prior to entering the oven. A consequence of spraying biocide on a finished product outside of the forming area is that the biocide does not find its way to the washwater in this situation.

Biocide may be applied in any suitable form, including as a solid, such as a tablet or powder; as a liquid, such as a solution or emulsion, suspension or other dispersion; or even potentially as a gas. The efficiency of one form relative to the others will depend largely on the amount and type of bacteria or organisms in the recycle water system, and on how the particular biocide is supplied. It is generally thought that addition of biocide in liquid form is most efficient in most situations.

Biocides of the same or different category may be introduced at any or each of the different locations; for example, a fungicide might be applied directly to finished product, whereas a bacteriocide is applied to washwater, directly or indirectly. In addition, in some embodiments, binder ingredients, compositions or dispersions may contain biocide of sufficient category and amount to be effective in these mixtures and in the finished product, while additional biocide of the same or different category may be supplemented in the washwater to control unwanted organisms there.

The biocide may be present in an amount from about 0.001% to about 10.0% by weight, depending on the location. Generally it is highest in the raw ingredients and/or binder composition, so that dilution of these into a sprayable dispersion causes an appropriate concentration without further adjustment. Some typical ranges by location are given in Table B, below, it being understood that all percentages are wt/wt and are modified by "about".

TABLE B

Typical biocide target concentrations by location

| System or location | Broad range | Intermediate Range | Target Range |
|---|---|---|---|
| Raw ingredients (dry) | 0.05% to 10.0% | 0.1% to 5% | 0.25% to 0.75% |
| Binder Compositions (dry) | 0.05% to 10.0% | 0.1% to 5% | 0.25% to 0.75% |
| Binder dispersions (wet) | 0.005% to 1.0% | 0.01% to 0.5% | 0.02% to 0.05% |
| Cleaning sprays (wet) | 0.01% to 0.5% | 0.02% to 0.3% | 0.05% to 0.1% |
| Stored washwater (wet) | 0.01% to 0.5% | 0.02% to 0.3% | 0.05% to 0.1% |

% given is wt/wt on a dry weight basis for raw ingredients and binder compositions, but includes water weight for dispersions, sprays and washwater.

EXAMPLES

Example 1

Binder Biocide Trial

A trial is conducted to test certain biocides in a bio-based binder composition. The bio-based binder compositions and the respective biocides are set forth in Table 1, below. The biocide is mixed with bio-based binder dispersions to a target concentration of about 0.5% on binder solids, approximately at the midpoint of the ranges given in Table 2. A bio-based binder dispersion is prepared having approximately 9% binder solids, and this is applied to glass fibers during the manufacture of insulation blankets at a rate to deliver about 6% LOI binder levels in the finished product. LOI, or loss on ignition, is a well known weight-by-difference analysis for the content of organic binder that can be burned off of glass fibers.

TABLE 1

Biocides and/or Preservatives in bio-based binders

| Sample | Binder . . . | with additive of: | Biocide | Preservative | ASTM C1338 | ASTM G21 |
|---|---|---|---|---|---|---|
| L-170 | Phenolic Control | | | | x | x |
| L-175-C | 80:20 MD-Acumer | | | | x | x |
| L-175-B | 80:20 MD-Acumer | w/ Fungitrol | x | | x | x |
| L-176-C | 80:20 MDCA w/5% SHP | | | | x | x |
| L-176-B | 80:20 MDC w/5% SHP | w/Amical) | x | | x | x |
| L-179-C | 80:20 MD-Acumer | | | | x | x |
| L-179-B | 80:20 MD-Acumer | w/Sodium Benzoate | | x | x | x |

TABLE 1-continued

Biocides and/or Preservatives in bio-based binders

| Sample | Binder . . . | with additive of: | Biocide | Preservative | ASTM C1338 | ASTM G21 |
|---|---|---|---|---|---|---|
| L-180-B | 80:20 MDCA w/5% SHP | w/Potassium Sorbate |  | x | x | x |
| L-181-B | 80:20 MD-Acumer | w/Spectrus NX100 | x |  | x | x |
| L-193-C | 80:20 MDCA w/5% SHP |  |  |  | x | x |

MD = Maltodextrin; CA = Citric Acid; SHP = Sodium Hypophosphite; Acumer = a polyacrylic acid available from Dow Chemical.

TABLE 2

Binder and biocide application rates and concentrations

| Biocide | Chemical name | % Active (as rec'd) | Target % Active in Binder | Target % Active in Washwater |
|---|---|---|---|---|
| Microban IC3 | 3-iodo-2propyl-n-butylcarbamate | 15-25% | 0.1-1.0% | .03-0.3% |
| ISP Fungitrol ™ | 3-Iodo-2-Propynyl Butylcarbamate | 35-45% | 0.1-1.0% | .03-0.3% |
| Spectrus NX100 | 2-bromo-2-nitro propane-1,3-diol (BNP); + 5-chloro-2-methyl-4-isothiazolin-3-one + magnesium nitrate and magnesium chloride | 10-30% | 0.1-1.0% | .03-0.3% |
| EnViro Bromax 7.1 | sulfamic acid, N-bromo, sodium salt | 15-30% | 0.1-1.0% | .03-0.3% |
| Dow Amical | diiodomethyl-p-tolysulfone | 36-44% | 0.1-1.0% | .03-0.3% |
| Nalcon 7649 | 2-bromo-2-nitropropane-1,3-diol (BNP); dibromoacetonitrile; | 10-35% | 0.1-1.0% | .03-0.3% |

After curing and an incubation period of 28 days, the resulting final insulation products are tested according to ASTM G21 and ASTM C1338 for the development of mold (see Example 2). ASTM Method G21 is designed to test for the growth of fungi in polymeric substances, such as a bio-based binder compositions or products, whereas ASTM Method C1338 is designed to test for the growth of fungi in complete insulation products and kraft papers.

Example 2

Binder Biocide Results

For ASTM Method G21, five fungal cultures are used *Aspergillus niger* (American Type Culture Collection #9642), *Penicillium pinophilum* (ATCC 11797), *Chaetomium globosum* (ATCC 6205), *Gliocladium virens* (ATCC 9645) and *Aureobasidium pullulans* (ATCC 15233). Spore suspensions of each of the five fungi were prepared and tested for viability.

Nutrient salts agar is poured into sterile dishes to provide a solidified agar layer from 3-6 mm in depth. Test specimens are cut from insulation products. All tests are run in triplicate. After the agar is solidified, the specimens are placed on the surface of the agar. The surfaces of the test specimens are sprayed with the composite spore suspension. The inoculated test specimens were incubated at 28-30° C. at a relative humidity of not less than 85%. The specimens were examined using a 40× microscope. The results and rating description are given in Table 3, below.

For ASTM Method C1338, five fungal cultures are used: *Aspergillus niger* (American Type Culture Collection 9642), *Aspergillus versicolor* (ATCC 11730), *Chaetomium globosum* (ATCC 6205), *Aspergillus flavus* (ATCC 9643) and *Penicillium funiculosum* (ATCC 11 797). The cultures were harvested as described and used to prepare the mixed spore suspension.

The viability of each fungal culture was confirmed. Inoculum viability controls were inoculated along with the test materials and comparative controls (white Birch tongue depressors, 20×150 mm, to simulate wood framing structures). After pre-conditioning, the samples and controls were inoculated in duplicate with the mixed fungal spore suspension. Inoculation was accomplished by spraying the suspension in the form of a fine mist from an atomizer. The test materials were sprayed until the initiation of droplet coalescence. Incubation was conducted at 86±4° F. and relative humidity of 95±4% RH for 28 days.

The inoculum and strain controls were examined after seven days of incubation. The samples and comparative controls were evaluated on the 28th day of testing using a binocular stereoscopic microscope (160 times magnification). Results are given in Table 3, below

TABLE 3

Fungal growth per ASTM G21 and ASTM C1338

| Sample | Fungal growth ASTM G-21 | Fungal growth ASTM C-1338 |
|---|---|---|
| L170-C | 0, 0, 0 | 0, 0 |
| L175-C | 0, 0, 0 | 0, 0 |
| L175-B | 0, 0, 0 | 0, 0 |
| L176-C | 0, 0, 0 | 0, 0 |
| L176-B | +, 0, 0 | 0, 0 |
| L179-B | 0, 0, 0 | 0, 0 |
| L180-B | +, +, 0 | +, + |

TABLE 3-continued

Fungal growth per ASTM G21 and ASTM C1338

| Sample | Fungal growth ASTM G-21 | Fungal growth ASTM C-1338 |
|--------|-------------------------|---------------------------|
| L181-B | 0, 0, 0                 | 0, 0                      |
| L193-C | 0, 0, 0                 | +, +                      |

Rating Legend:
0 = none or no growth;
1 or + = scant or trace growth (<10%);
2 or ++ = light to moderate growth (10-30%);
3 or +++ = medium to heavy growth (30-60%); and
4 or ++++ = heavy to confluent growth (60-100%)

As seen in Table 3, all test specimens passed and most test samples did not support fungal growth at all. Samples L176-B (w/Amical) and L180-B (w/potassium sorbate) supported traces of growth that covered less than 1% of the surface areas in the ASTM G21 Method.

In the ASTM 1338 Method, all fungal strain viability controls and the inoculum (at 28 days) showed copious amounts of fungal growth indicating a valid fungal resistance test. The comparative Birch controls showed slight fungal growth covering 80% of the surface area (++ growth). All samples pass the ASTM C1338 fungal resistance test as the fungal growth observed does not exceed the fungal growth on the standard control test item. It should be noted that the fungal growth on samples L180-B (w/potassium sorbate) and L193-C (control with no biocide) was scant and covered less than 0.5% of the test surface.

Example 3

Washwater Biocide Trial

An isothiazoline based biocide (PMC T-360) is added to the washwater of a manufacturing plant for the manufacture of fiberglass insulation products. Illustrative biocides and target concentration levels for use in washwater are also presented in Table 2 above.

Bacterial counts of this washwater have been estimated by various methodologies. Initially, counts were based on the growing of cultures and the cultures are plated to determining the concentration of colony forming units, or CFU/ml. Without biocide, the counts quickly get quite high, at times exceeding $10^6$ CFU/ml, which causes considerable odor. By the addition of biocide as described above, counts could be maintained within an acceptable level of between $10^2$ and $10^3$ CFU/ml.

Alternative methodologies include using a bioilluminescence/ATP method, but colorants used in the binder may complicate interpretation. This method can give bacterial results in minutes as compared to cultures that require 3 days. Also, incubated dip slide testing is another fairly rapid means to estimate bacterial counts.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for the recitation of the claims set forth below.

What is claimed is:

1. A fibrous, mineral fiber insulation product comprising:
a plurality of randomly oriented mineral fibers; and
a binder composition applied to at least a portion of the randomly oriented mineral fibers, the binder composition including:
maltodextrin having a dextrose equivalent number from 9 to 14, the maltodextrin comprising from 40% to 95% by weight of total solids of the binder composition;
at least one crosslinking agent selected from a monomeric polycarboxylic acid, citric acid, or their corresponding salts, the at least one crosslinking agent comprising from 5% to 40% of total solids of the binder composition, the at least one crosslinking agent having a number average molecular weight ranging from 90 to 10,000; and
a biocide in an amount up to 10% by weight of total solids of the binder composition.

2. The fibrous, mineral fiber insulation product of claim 1, wherein the at least one crosslinking agent has a number average molecular weight ranging from 190 to 4,000.

3. The fibrous, mineral fiber insulation product of claim 2, wherein the at least one crosslinking agent has a number average molecular weight ranging from 190 to 1,000.

4. The fibrous, mineral fiber insulation product of claim 1, wherein the at least one crosslinking agent is selected from citric acid, a salt thereof, and combinations thereof.

5. A fibrous, glass fiber insulation product comprising:
a plurality of randomly oriented glass fibers; and
a thermoset, bio-based binder composition applied to at least a portion of the randomly oriented glass fibers, the bio-based binder composition including:
maltodextrin having a number average molecular weight from 1,000 to 8,000 and a dextrose equivalent number ranging from no less than 9 to no more than 14;
at least one crosslinking agent consisting of citric acid, the at least one crosslinking agent comprising from about 5% to about 40% of total solids of the bio-based binder composition, the at least one crosslinking agent having a number average molecular weight ranging from 90 to 10,000; and
a biocide in an amount from 0.05% to 10% by weight by weight of binder solids.

6. The fibrous, mineral fiber insulation product of claim 1, wherein the biocide is present in an amount from 0.05% to 1.0% by weight of total solids of the binder composition.

7. The fibrous, mineral fiber insulation product of claim 6, wherein the biocide is present in an amount from 0.1% to 0.5% by weight of total solids of the binder composition.

8. The fibrous, mineral fiber insulation product of claim 1, wherein the biocide comprises one or more of:
3-iodo-2propyl-n-butylcarbamate;
carbamic acid, butyl-3-iodo-2-propynyl ester (IPBC);
2-bromo-2-nitropropane-1,3-diol, magnesium nitrate, 5-chloro-2-methyl-4-isothiazolin-3-one, magnesium chloride;
sulfamic acid, N-bromo, sodium salt;
diiodomethyl-p-tolysulfone;
dibromoacetonitrile; and
2,2-dibromo-3-nitrilopropionamide.

9. The fibrous, glass fiber insulation product of claim 5, wherein the bio-based binder composition comprises citric acid as the sole crosslinking agent, and the biocide comprises one or more of sodium bromide and an isothiazolin class biocide.

10. The fibrous, glass fiber insulation product of claim 9, wherein the biocide comprises 5-chloro-2-methyl-4-isothiazolin-3-one.

\* \* \* \* \*